United States Patent
Bruun

(10) Patent No.: US 11,166,935 B2
(45) Date of Patent: Nov. 9, 2021

(54) CANNABINOID POUCH

(71) Applicant: NordicCan A/S, Vejle (DK)

(72) Inventor: Heidi Ziegler Bruun, Vejle Ost (DK)

(73) Assignee: NordicCan A/S

(*) Notice: Subject to any disclaimer, the term of this patent is extended or adjusted under 35 U.S.C. 154(b) by 0 days.

(21) Appl. No.: 16/626,166

(22) PCT Filed: Jun. 23, 2017

(86) PCT No.: PCT/DK2017/050210
§ 371 (c)(1),
(2) Date: Dec. 23, 2019

(87) PCT Pub. No.: WO2018/233782
PCT Pub. Date: Dec. 27, 2018

(65) Prior Publication Data
US 2020/0179329 A1    Jun. 11, 2020

(51) Int. Cl.
| | | |
|---|---|---|
| *A61K 31/352* | (2006.01) | |
| *A61K 9/00* | (2006.01) | |
| *A61K 47/26* | (2006.01) | |
| *A61K 47/12* | (2006.01) | |
| *A61K 31/05* | (2006.01) | |

(52) U.S. Cl.
CPC ............ *A61K 31/352* (2013.01); *A61K 9/009* (2013.01); *A61K 9/0056* (2013.01); *A61K 31/05* (2013.01); *A61K 47/12* (2013.01); *A61K 47/26* (2013.01)

(58) Field of Classification Search
None
See application file for complete search history.

(56) References Cited

U.S. PATENT DOCUMENTS

| | | |
|---|---|---|
| 2013/0098377 A1 | 4/2013 | Borschke et al. |
| 2015/0057342 A1* | 2/2015 | Koren .................. A61K 31/047 514/454 |
| 2016/0015683 A1 | 1/2016 | McCarty |
| 2016/0165953 A1* | 6/2016 | Goode, Jr. ............. A24B 13/00 131/352 |
| 2016/0220593 A1 | 8/2016 | Anastassov et al. |
| 2017/0172927 A1 | 6/2017 | Fusco et al. |

FOREIGN PATENT DOCUMENTS

| | | | |
|---|---|---|---|
| WO | 2015117011 A1 | 8/2015 | |
| WO | WO-2015117011 A1 * | 8/2015 | ............. A23L 27/36 |
| WO | 2017059859 A1 | 4/2017 | |
| WO | 2018233781 A1 | 12/2018 | |

OTHER PUBLICATIONS

Remington's Pharmaceutical Sciences, 17th Edition, A.G. Gennaro, Editor, 1985, p. 655. (Year: 1985).*
Merriam Webster Dictionary online: Definition of "pouch." Downloaded Jan. 11, 2021 from https://www.merriam-webster.com/dictionary/pouch (Year: 2020).*
Merriam Webster Dictionary online: Definition of "sachet." Downloaded Jan. 8, 2021 from https://www.merriam-webster.com/dictionary/sachet. (Year: 2020).*

* cited by examiner

*Primary Examiner* — Michael P Cohen
(74) *Attorney, Agent, or Firm* — St. Onge Steward Johnston & Reens LLC

(57) ABSTRACT

A pouch designed for administration of an active ingredient in the oral cavity is disclosed, the pouch containing an amount of one or more cannabinoids. Also, pouches for use as a medicament, for use in alleviation of pain, and for use in mitigation of appetite deficiency are disclosed. Further, a method of alleviation of pain and a method of mitigation of appetite deficiency using the pouch are disclosed.

22 Claims, No Drawings

CANNABINOID POUCH

FIELD OF THE INVENTION

The invention relates to pouches comprising cannabinoids.

BACKGROUND OF THE INVENTION

Cannabinoids or derivatives thereof have been used for medical purposes.

Cannabis is often administering by smoking. A problem related to such administration is that the rapid absorption into the blood via the lung may be undesirable. Not only may the smoking as such have side effects, but the administration may be difficult to manage.

SUMMARY OF THE INVENTION

The invention relates to a pouch designed for administration of an active ingredient in the oral cavity, the pouch containing an amount of one or more cannabinoids.

According to the invention, the pouch comprises one or more cannabinoids as the active ingredient. One advantage of the invention may be that a more controllable release of said one or more cannabinoids may be obtained. Particularly, when using a matrix composition comprising a water-soluble composition, a relatively fast and complete release of said one or more cannabinoids may be obtained. One example thereof is when the water-soluble composition is used as a carrier for the one or more cannabinoids, thus directly influencing the release of the one or more cannabinoids and facilitating an essentially complete release of the one or more cannabinoids as a water-soluble carrier.

Moreover, the matrix composition may comprise further enhancers or substances modifying the release. Examples of such substances include water-solubility modifiers, which may e.g. prolong the release time.

According to an advantageous embodiment of the invention said one or more cannabinoids are provided in a matrix composition, and wherein said matrix composition further comprise a water-soluble composition.

An advantage of the above embodiment may be that by providing the one or more cannabinoids with a water-soluble composition, especially when used as a carrier, the one or more cannabinoids may be released relatively fast, thereby reaching a delivery in the oral cavity of the predefined labelled total dose of cannabinoids in a relatively fast manner. Obtaining a fast release of cannabinoids to the labelled dose is advantageous e.g. when using the pouch for medical purposes, where knowing the exact delivered dose may help e.g. to evaluate if the dose was too high or too low and/or to account for intake of drugs, food etc. When providing the intake of cannabinoids by smoking cannabis, the specific intake of cannabinoids is typically much more dependent on user behavior and thus more unpredictable, especially for persons other than the user, such as for medical staff.

Obtaining a more or less complete release in a relatively short time frame thus allows both the user of the pouch and any medical staff to know, relatively accurately, the dosage of the one or more cannabinoids, which have been delivered to the user. Also, when pouch is completely emptied by use, it may thus be possible to know when the delivery of the one or more cannabinoids to the oral cavity ended, especially when the release of the one or more cannabinoids is synchronized with the release of the remaining part of the matrix composition, i.e. the remaining content of the pouch.

According to an advantageous embodiment of the invention the matrix composition comprises said water-soluble composition in an amount of between 1 and 99 percent weight of said matrix composition.

According to an embodiment of the invention, the matrix composition comprises said water-soluble composition in an amount of between 2 and 95 percent weight of said matrix composition.

According to an embodiment of the invention, the matrix composition comprises said water-soluble composition in an amount of between 20 and 99 percent weight of said matrix composition.

According to an embodiment of the invention, the matrix composition comprises said water-soluble composition in an amount of between 3 and 80 percent weight of said matrix composition.

According to an embodiment of the invention, the matrix composition comprises said water-soluble composition in an amount of between 2 and 70 percent weight of said matrix composition.

According to an embodiment of the invention, the matrix composition comprises said water-soluble composition in an amount of between 5 and 50 percent weight of said matrix composition.

According to an embodiment of the invention, the pouch consists of said matrix composition and a sealed barrier enclosing said matrix composition.

According to an advantageous embodiment of the invention the water-soluble composition comprises a water-soluble carrier.

One advantage of the above embodiment may be that a relatively precise and predictive dosage of cannabinoids may be delivered to a user. By utilizing a water-soluble carrier facilitating the release of cannabinoids, the predictable release may be obtained since the complete amount of cannabinoids may be released. I.e. by ensuring an exact total dosage of cannabinoids comprised in the pouched product, the same dosage of cannabinoids will be released in the oral cavity. The complete release of cannabinoids may be obtained by a relatively fast release, i.e. such that within a typical usage time period of e.g. 10 minutes, the complete amount of cannabinoids and carrier is released to the oral cavity.

Moreover, the pouched product may be left completely empty after the total amount of cannabinoids and carrier has been released to the oral cavity thus allowing the user to confirm in an intuitive manner that the complete release was obtained.

A further advantage may be that a relatively effective and/or fast uptake of cannabinoids may be provided, due to a local high concentration around the pouch, thereby giving a relatively steep concentration gradient across the mucous membrane.

According to an embodiment of the invention, the pouch comprise a further active ingredient other than said one or more cannabinoids.

According to an embodiment of the invention, the water-soluble composition is a water-soluble carrier.

One significant advantage of the above embodiment may be that the release of the water-soluble composition as the carrier is synchronized, at least to a relatively high degree, with the release of said one or more cannabinoids.

According to an advantageous embodiment of the invention the water-soluble composition comprises sugar alcohol.

According to an embodiment of the invention, said sugar alcohol may be a single type of sugar alcohol, or a mixture of two or more sugar alcohols.

One advantage of the above embodiment may be that sugar alcohols have excellent properties with respect to water solubility and also that it does contribute to teeth decay. Furthermore, it provides sweetening thus it contributed to masking the taste of said one or more cannabinoids. Especially when the release of the one or more cannabinoids is synchronized with the sugar alcohols, e.g. by using the sugar alcohols as a carrier for the one or more cannabinoids, an effective taste masking contribution by the sugar alcohols may be obtained.

In embodiments, where the water-soluble composition comprises or is a water-soluble carrier, the sugar alcohol may be the water-soluble carrier or part thereof.

According to an advantageous embodiment of the invention the matrix composition comprises sugar alcohol in an amount of 1-99 percent by weight of said matrix composition.

According to an embodiment of the invention the matrix composition comprises sugar alcohol in an amount of 20-99 percent by weight of said matrix composition, or in an amount of 20-90 percent by weight of said matrix composition.

According to an embodiment of the invention the sugar alcohol forms a carrier.

According to an advantageous embodiment of the invention said sugar alcohol is selected from the group consisting of sorbitol, erythritol, xylitol, lactitol, maltitol, mannitol, hydrogenated starch hydrolyzates, isomalt, or any combination thereof.

According to an advantageous embodiment of the invention the water-soluble composition is sugar alcohol.

According to an advantageous embodiment of the invention the water-soluble composition comprises sugar.

According to an advantageous embodiment of the invention the matrix composition comprises sugar in an amount of 1-99 percent by weight of said matrix composition.

According to an embodiment of the invention the matrix composition comprises sugar in an amount of 20-99 percent by weight of said matrix composition, or in an amount of 20-90 percent by weight of said matrix composition.

According to an embodiment of the invention, the sugar is chosen from the group consisting of sucrose, dextrose, maltose, dextrins, trehalose, D-tagatose, dried invert sugar, fructose, levulose, galactose, corn syrup solids, and combinations thereof.

According to an embodiment of the invention, the water-soluble composition comprises a combination of sugar and sugar alcohol.

According to an advantageous embodiment of the invention the one or more cannabinoids are present in granules of the water-soluble matrix composition.

According to an embodiment of the invention the granules comprises the water-soluble composition as a carrier in combination said one or more cannabinoids, optionally in combinations with further substances, such as flavor etc.

According to an advantageous embodiment of the invention the matrix composition further comprises a release controlling composition.

One advantage of the above embodiment may be that by controlling the release of the one or more cannabinoids, e.g. by means of controlling the supply of water in the form of saliva to the matrix composition, a modified release may be obtained, e.g. a delayed release.

According to an advantageous embodiment of the invention said release controlling composition is selected from the list consisting of metallic stearates, modified calcium carbonate, hydrogenated vegetable oils, partially hydrogenated vegetable oils, polyethylene glycols, polyoxyethylene monostearates, animal fats, silicates, silicates dioxide, talc, magnesium stearates, calcium stearates, fumed silica, powdered hydrogenated cottonseed oils, hydrogenated vegetable oils, hydrogenated soya oil and mixtures thereof.

According to an advantageous embodiment of the invention the release controlling composition is hydrophobic.

One advantage of the above embodiment may be that an effective control of the supply of water in the form of saliva may be obtained, thus giving control of the release.

According to an advantageous embodiment of the invention said release controlling composition comprises one or more metallic stearates.

One advantage of the above embodiment may be that metallic stearates, such as calcium stearate or magnesium stearate, may be highly suitable for obtaining the desired release of said one or more cannabinoids. Metallic stearates are examples of hydrophobic release controlling compositions.

According to an advantageous embodiment of the invention said release controlling composition comprises magnesium stearate.

According to an advantageous embodiment of the invention said release controlling composition comprises calcium stearate.

According to an advantageous embodiment of the invention the matrix composition comprises said release controlling composition in an amount of between 1 and 20 percent by weight of said matrix composition.

According to an embodiment of the invention the matrix composition comprises said release controlling composition in an amount of between 3 and 15 percent by weight of said matrix composition.

According to an advantageous embodiment of the invention the water-soluble composition is a powder composition.

For example, when the water-soluble composition is a water-soluble carrier, it may be provided as a powder composition.

According to an advantageous embodiment of the invention the matrix composition is a powdered matrix composition.

According to an advantageous embodiment of the invention said powdered matrix composition has an average particle size of below 1200 micrometer.

According to an advantageous embodiment of the invention wherein said powdered matrix composition has an average particle size of above 1 micrometer.

According to an embodiment of the invention, the powdered matrix composition as an average particle size is between 1 and 1200 micrometer.

In an embodiment of the invention the powdered matrix composition has an average particle size of said powdered composition is between 1 and 400 micrometers.

According to an embodiment of the invention, the average powder diameter is larger than the average opening dimension of the pouch.

According to an embodiment of the invention the characteristic opening dimension is adapted to the characteristic dimension of the matrix composition so as to retain the matrix composition inside the pouch before use.

According to an advantageous embodiment of the invention the pouch comprises a water-permeable membrane, comprising e.g. woven or non-woven fabric.

According to an advantageous embodiment of the invention the one or more cannabinoids are on crystalline form.

According to an embodiment of the invention, the one or more cannabinoids comprises cannabidiol or consists of cannabidiol on crystalline form.

According to an advantageous embodiment of the invention the one or more cannabinoids are physically or chemically bound to at least part of the matrix composition acting as a carrier.

According to an advantageous embodiment of the invention the one or more cannabinoids have been granulated with the carrier.

According to an advantageous embodiment of the invention the matrix composition comprises said one or more cannabinoids in an amount of between 0.1 and 50 percent weight of said matrix composition.

In embodiments, where a cannabinoid extract is used as a source of said one or more cannabinoids, the matrix composition may in some cases comprise a lower amount of cannabinoids, such as e.g. 0.1 to 30 percent by weight of the matrix composition, especially when a relatively diluted extract is used, i.e. where the content of cannabinoids is relatively low.

According to an advantageous embodiment of the invention the matrix composition comprises said one or more cannabinoids in an amount of 0.25 to 500 milligrams.

According to an advantageous embodiment of the invention said one or more cannabinoids are derived from cannabis.

In an alternative embodiment, the composition may comprise one or more cannabinoids, where one or all of the cannabinoids are not derived from cannabis, and e.g. comprise synthetic cannabinoids.

According to an advantageous embodiment of the invention said one or more cannabinoids comprises at least two cannabinoids.

According to an advantageous embodiment of the invention said one or more cannabinoids consists of two cannabinoids.

Thus, according to the above embodiment, the matrix composition and the pouch is substantially free of further cannabinoids other than said two cannabinoids. Moreover, it should be understood according to the above embodiment that the pouch comprises a combination of two cannabinoids, i.e. a combination of two different types of cannabinoids. Further, the pouch according to the above embodiment comprises only two cannabinoids. In practical scenarios, it may not be easy to achieve complete elimination of certain substances, thus, there may in some embodiments be small or trace amounts of further cannabinoids, e.g. due to a small degree of degradation of the intended cannabinoid(s).

According to an advantageous embodiment of the invention said one or more cannabinoids consists of one cannabinoid, such as tetrahydrocannabinol or cannabidiol.

According to an advantageous embodiment of the invention the one or more cannabinoids comprise cannabidiol.

According to an advantageous embodiment of the invention said one or more cannabinoids comprises cannabidiol in an amount of between 10 and 100 percent by weight of the one or more cannabinoids.

In an embodiment of the invention the one or more cannabinoids comprises cannabidiol in an amount of between 20 and 100 percent by weight of the one or more cannabinoids.

In an embodiment of the invention the one or more cannabinoids comprises cannabidiol in an amount of between 30 and 90 percent by weight of the one or more cannabinoids.

In an embodiment of the invention the one or more cannabinoids comprises cannabidiol in an amount of between 50 and 90 percent by weight of the one or more cannabinoids.

In an embodiment of the invention the one or more cannabinoids comprises cannabidiol in an amount of between 70 and 99 percent by weight of the one or more cannabinoids.

In one embodiment, the one or more cannabinoids consists essentially of cannabidiol.

According to an advantageous embodiment of the invention the one or more cannabinoids comprise tetrahydrocannabinol.

According to an advantageous embodiment of the invention the one or more cannabinoids comprises tetrahydrocannabinol in an amount of between 10 and 100 percent by weight of the one or more.

In an embodiment of the invention the one or more cannabinoids comprises tetrahydrocannabinol in an amount of between 20 and 100 percent by weight of the one or more cannabinoids.

In an embodiment of the invention the one or more cannabinoids comprises tetrahydrocannabinol in an amount of between 30 and 90 percent by weight of the one or more cannabinoids.

In an embodiment of the invention the one or more cannabinoids comprises tetrahydrocannabinol in an amount of between 50 and 90 percent by weight of the one or more cannabinoids.

In an embodiment of the invention the one or more cannabinoids comprises tetrahydrocannabinol in an amount of between 70 and 99 percent by weight of the one or more cannabinoids.

In one embodiment, the one or more cannabinoids consists essentially of tetrahydrocannabinol.

According to an advantageous embodiment of the invention the pouch comprises a humectant.

In one embodiment, the humectant may be the water-soluble composition or be part of the water-soluble composition, whereas in other embodiments it may be provided as a separate composition in the pouch. When the water-soluble composition comprises a carrier or is part of a carrier, the humectant may be provided as the water-soluble carrier or as a separate composition in the pouch.

Suitable humectants may include one or more hygroscopic materials, such as cellulose, sugar alcohols, and other hygroscopic materials.

According to an advantageous embodiment of the invention the humectant comprises one or more from the list consisting of sugar alcohols, alginate, cellulose, such as microcrystalline cellulose, pectin, xanthan gum.

The humectant may in one embodiment be provided separately from the water-soluble composition.

The humectant may in one embodiment be provided by the water-soluble composition, i.e. the water-soluble composition is a humectant or comprises a humectant. When the water-soluble composition comprises a carrier, or is part of a carrier, the carrier may be a humectant.

The invention further relates to pouch according to the invention or any of its embodiments for use as a medicament.

The invention further relates to pouch according to the invention or any of its embodiments for use in alleviation of pain.

According to an advantageous embodiment of the invention said pain is neurotic pain According to an advantageous embodiment of the invention said pain is cancer-related pain.

The invention further relates to a pouch according to the invention or any of its embodiments for use in mitigation of appetite deficiency.

The invention further relates to a method of alleviation of pain, such as neurotic pain or cancer-related pain, by administering an effective amount of said one or more cannabinoids by means of the pouch according to the invention or any of its embodiments.

The invention further relates to a method of mitigation of appetite deficiency by administering an effective amount of said one or more cannabinoids by means of the pouch according to the invention or any of its embodiments.

DETAILED DESCRIPTION OF THE INVENTION

Definitions

As used herein the term "pouch" is intended to mean a container typically formed by a web of a fibrous material enclosing a cavity. The pouch is pouch designed for administration of an active ingredient in the oral cavity, and thus it is adapted for oral use, it is non-toxic and not water-soluble. The fibrous material may e.g. form a woven or non-woven web or fabric. The pouch may for example be sealed by bonding two corresponding pieces of web or fabric to each other along their edges to form a cavity for the one or more cannabinoids and the non-water-soluble composition. In order to release the one or more cannabinoids, the pouch is made water-permeable so as to allow saliva from the oral cavity to penetrate the pouch and enter the cavity, where the saliva can come into contact with the one or more cannabinoids, whereby the one or more cannabinoids are released from the oral pouch.

As used herein the term "carrier" is intended to mean a substance that binds, physically or chemically an active ingredient. Unless otherwise stated, the term "carrier" refers to a carrier for said one or more cannabinoids. Examples of carriers include water-soluble compositions, such as e.g. sugar alcohols. For example, the water-soluble compositions may be granulated with the one or more cannabinoids.

As used herein the term "cannabinoids" refers to cannabinoids derived from cannabis plants and synthetic cannabinoids. Examples of cannabinoids include cannabidiol, tetrahydrocannabinol, cannabinol, etc.

As used herein the terms "cannabidiol" and "CBD" both refer to Cannabidiol (IUPAC: 2-[(1R,6R)-6-isopropenyl-3-methylcyclohex-2-en-1-yl]-5-pentylbenzene-1,3-diol).

As used herein the terms "tetrahydrocannabinol" and "THC" both refer to Tetrahydrocannabinol, (−)-trans-Δ9-tetrahydrocannabinol (IUPAC: (−)-(6aR,10aR)-6,6,9-Trimethyl-3-pentyl-6a,7,8,10a-tetrahydro-6H-benzo[c]chromen-1-ol).

As used herein the term "powder composition" refers to composition in the form of powder, i.e. as a particulate material having a relatively small particle size, for example between 1 and 1200 micrometer.

As used herein the term "humectant" is understood as a moistening agent used to attract moisture or water in the form of saliva. Humectants may typically include suitably hygroscopic compositions. In some cases, humectants may also be described as moistening agents, due to their role in attraction of moisture. Examples of humectants include cellulose, such as microcrystalline cellulose and other cellulose types disclosed herein, sugar alcohols, such as those disclosed herein, alginate, cellulose, such as microcrystalline cellulose, pectin, xanthan gum, etc.

As used herein the term "water-soluble composition" refers to a composition having a relatively high water-solubility, for example consisting of water-soluble substances having a water-solubility of more than 5 gram of water-soluble composition per 100 mL of water measured at 25 degrees Celsius and pH of 7.0. When referring to an "soluble" composition or substance, water-soluble is meant, unless otherwise stated. Likewise, when referring to "insoluble", water-insoluble is meant unless otherwise stated. The water-soluble composition is part of the matrix composition. In some embodiments, the water-soluble composition is part of a carrier or forms such carrier.

As used herein the term "matrix composition" is used as reference to the total content of the pouch, i.e. the entire composition enclosed by the pouch. Typically, it therefore corresponds to the pouch excluding the outer membrane of the pouch. Furthermore, the term "matrix composition" is typically used as the content of the pouch whenever more than said one or more cannabinoids are present in the pouch.

Typically, the pouches comprises openings, where the characteristic opening dimension is adapted to a characteristic dimension of the matrix composition so as to retain the matrix composition inside the pouch before use and/or to retain a part of the matrix composition, such as an insoluble composition, inside the pouch during use.

In order to obtain a pouch having suitable opening dimensions in view of the matrix composition to be used, the material for the pouch may be selected accordingly, e.g. comprising e.g. woven or non-woven fabric.

In other words, according to the various embodiments, the pouch forms a membrane allowing passage of saliva and prevents or inhibits passage of said matrix composition. The membrane of the pouch may be of any suitable material e.g. woven or non-woven fabric (e.g. cotton, fleece etc.), heat sealable non-woven cellulose or other polymeric materials such as a synthetic, semi-synthetic or natural polymeric material. An example of suitable pouch material is paper made of pulp and a small amount of wet strength agent. A material suitable for use must provide a semi-permeable membrane layer to prevent the powder or composition from leaving the bag or pouch during use. Suitable materials are also those that do not have a significant impact on the release of cannabinoids from the pouch.

The powder is filled into pouches and is maintained in the pouch by a sealing. An ideal pouch is chemically and physically stable, it is pharmaceutically acceptable, it is insoluble in water, it is easy to fill with powder and seal, and it provides a semi-permeable membrane layer which prevent the powder from leaving the bag, but permit saliva and therein dissolved or sufficiently small suspended components from the powder in the pouch, such as cannabinoids, to pass through said pouch.

The pouch may be placed in the oral cavity by the user. Saliva then enters into the pouch, and the one or more cannabinoids and other components, which are soluble in saliva, start to dissolve and are transported with the saliva out of the pouch into the oral cavity, where the cannabinoid may be absorbed.

According to an embodiment of the invention, the matrix composition may further comprise one or more enhancers.

In an embodiment of the invention, said enhancers are selected from the group consisting of bile salts, cetomacrogols, chelating agents, citrates, cyclodextrins, detergents, enamine derivatives, fatty acids, labrasol, lecithins, phospholipids, syntetic and natural surfactants, nonionic surfactants, cell envelope disordering compounds, solvents, steroidal detergents, chelators, solubilization agents, charge modifying agents, pH control agents, degradative enzyme inhibitors, mucolytic or mucus clearing agents, membrane penetration-enhancing agents, modulatory agents of epithelial junction physiology, vasodilator agents, selective transport-enhancing agents, or any combination thereof. pH control agents include buffers.

In an embodiment of the invention, said enhancers are selected from the group consisting of cetylpyridinium chloride (CPC), benzalkonium chloride, sodium lauryl sulfate, polysorbate 80, Polysorbate 20, cetyltrimethylammonium bromide, laureth 9, sodium salicylate, sodium EDTA, EDTA, aprotinin, sodium taurocholate, saponins, bile salt derivatives, fatty acids, sucrose esters, azone emulsion, dextran sulphate, linoleic acid, labrafil, transcutol, urea, azone, nonionic surfactants, sulfoxides, sauric acid/PG, POE 23 lauryl ether, methoxysalicylate, dextran sulfate, methanol, ethanol, sodium cholate, Sodium taurocholate, Lysophosphatidyl choline, Alkylglycosides, polysorbates, Sorbitan esters, Poloxamer block copolymers, PEG-35 castor oil, PEG-40 hydrogenated castor oil, Caprocaproyl macrogol-8 glycerides, PEG-8 caprylic/capric, glycerides, Dioctyl sulfosuccinate, Polyethylene lauryl ether, Ethoxydiglycol, Propylene glycol, mono-di-caprylate, Glycerol monocaprylate, Glyceryl fatty acids (C$_8$-C$_{18}$) ethoxylated Oleic acid, Linoleic acid, Glyceryl caprylate/caprate, Glyceryl monooleate, Glyceryl monolaurate, Capryliccapric triglycerides, Ethoxylated nonylphenols, PEG-(8-50) stearates, Olive oil PEG-6, esters, Triolein PEG-6 esters, Lecithin, d-alpha tocopherol polyethylene glycol 1,000 succinate, Citric acid, Sodium citrate, BRIJ, Sodium laurate, 5-methoxysalicylic acid, Bile salts, Acetyl salicylate, ZOT, Docosahexaenoic acid, Alkylglycosides, Sodium glycocholate (GC-Na), Sodium taurocholate (TC-Na), EDTA, Choline salicylate, Sodium caprate (Cap-Na), N-lauryl-beta-D-maltopyranoside (LM), Diethyl maleate, Labrasol, Sodium salicylate, Mentol, Alkali metal alkyl sulphate, Sodium lauryl sulphate, Glycerin, Bile acid, Lecithin, phosphatidylcholine, phosphatidylserine, sphingomyelin, phophatidylethanolamine, cephalin, lysolecithin, Hyaluronic acid: alkalimetal salts, sodium, alkaline earth and aluminum, Octylphenoxypolyethoxyethanol, Glycolic acid, Lactic acid, Chamomile extract, Cucumber extract, Borage oil, Evening primrose oil, Polyglycerin, Lysine, Polylysine, Triolein, Monoolein, Monooleates, Monolaurates, Polydocanol alkyl ethers, Chenodeoxycholate, Deoxycholate, Glycocholic acid, Taurocholic acid, Glycodeoxycholic acid, Taurodeoxycholic acid, Sodium glycocholate, Phosphatidylcholine, Phosphatidylserine, Sphingomyelin, Phosphatidylethanolamine, Cephalin, Lysolecithin, Alkali metal hyaluronates, Chitosan, Poly-L-arginine, Alkyl glucoside, Saccharide alkyl ester, Fusidic acid derivatives, Sodium taurdihydrofusidate (STDHF), L-α-phosphatidylcholine Didecanoyl (DDPC), Nitroglycerine, nitropruside, NOC5 [3-(2-hydroxy-I-(methyl-ethyl)-2-nitrosohydrazino)-I-propanamine], NOC12 [iV-ethyl-2-(I-ethyl-hydroxy-2-nitrosohydrazino)-ethanamine, SNAP [S-nitroso-N-acetyl-DL-penicillamine, NORI, NOR4, deacylmethyl sulfoxide, azone, salicylamide, glyceryl-I,3-diacetoacetate, I,2-isopropylideneglycerine-3-acetoacetate), Amino acids, Amino acid salts, monoaminocarboxlic acids, Glycine, alanine, phenylalanine, proline, hydroxyproline, hydroxyamino acids, serine, acidic amino acids, aspartic acid, Glutamic acid, Basic amino acids, Lysine, N-acetylamino acids, N-acetylalanine, N-acetylphenylalanine, TM-acetylserine, N-acetylglycine, N-acetyllysine, N-acetylglutamic acid, N-acetylproline, N-acetylhydroxyproline, lactic acid, malic acid and citric acid and alkali metal salts thereof, pyrrolidonecarboxylic acids, alkylpyrrolidonecarboxylic acid esters, N-alkylpyrrolidones, proline acyl esters, sodium lauryl phosphate, sodium lauryl sulphate, sodium oleyl phosphate, sodium myristyl sulphate, polyoxyethylene alkyl ethers, polyoxyethylene alkyl esters, and caproic acid, alkylsaccharide, fusidic acid, polyethylene glycol, cetyl alcohol, polyvinylpyrolidone, Polyvinyl alcohol, Lanolin alcohol, Sorbitan monooleate, Ethylene glycol tetraacetic acid, Bile acid conjugate with taurine, Cholanic acid and salts, Cyclodextran, Cyclodextrin, Cyclodextrin (beta), Hydroxypropyl-β-cydodetran, Sulfobutylether-β-cyclodextran, Methyl-β-cyclodextrin, Chitosan glutamate, Chitosan acetate, Chitosan hydrochloride, Chitosan hydrolactate, 1-O-alkyl-2-hydroxy-sn-glycero-3-phosphocholine, 3-O-alkyl-2-acetoyl-sn-glycero-1-phosphocholine, 1-O-alkyl-2-O-acetyl-sn-glycero-3-phospho(N,N,N-trimethyl)hexanolamine, Propylene glycol, Tetradecylmaltoside (TDM), Sucrose dedecanoate.

According to an embodiment of the invention, the enhancer comprises one or more pH control agent, such as a buffering agent.

In an embodiment of the invention, said pH control agents are selected from the group consisting of Acetic acid, Adipic acid, Citric acid, Fumaric acid, Glucono-δ-lactone, Gluconic acid, Lactic acid, Malic acid, Maleic acid, Tartaric acid, Succinic acid, Propionic acid, Ascorbic acid, Phosphoric acid, Sodium orthophosphate, Potassium orthophosphate, Calcium orthophosphate, Sodium diphosphate, Potassium diphosphate, Calcium diphosphate, Pentasodium triphosphate, Pentapotassium triphosphate, Sodium polyphosphate, Potassium polyphosphate, Carbonic acid, Sodium carbonate, Sodium bicarbonate, Potassium carbonate, Calcium carbonate, Magnesium carbonate, Magnesium oxide, or any combination thereof.

According to various embodiments of the invention, one or more sugar alcohols may be included in the pouch as part of the matrix composition, e.g. as a carrier or part thereof, as a humectant, or as a sweetener. Suitable sugar alcohols include sugar alcohols selected from the group of sorbitol, erythritol, xylitol, lactitol, maltitol, mannitol, hydrogenated starch hydrolyzates, isomalt, or any combination thereof.

In an embodiment of the invention the pouch comprises high intensity sweetener.

Preferred high intensity sweeteners include, but are not limited to sucralose, aspartame, salts of acesulfame, such as acesulfame potassium, alitame, saccharin and its salts, cyclamic acid and its salts, glycyrrhizin, dihydrochalcones, thaumatin, monellin, stevioside and the like, alone or in combination.

In an embodiment of the invention, the pouch comprises bulk sweeteners including sugar and/or sugarless components.

In an embodiment of the invention, the pouch comprises bulk sweetener in the amount of 5 to about 95% by weight of the pouch, more typically constitute 20 to about 80% by weight of the pouch, and more commonly, 30 to 60% by weight of the pouch. Bulk sweeteners may function both as a sweetener and also as a humectant.

The sweeteners may often support the flavor profile of the pouch.

Sugar sweeteners generally include, but are not limited to saccharide-containing components commonly known in the art of pouches, such as sucrose, dextrose, maltose, saccharose, lactose, sorbose, dextrin, trehalose, D-tagatose, dried invert sugar, fructose, levulose, galactose, corn syrup solids, glucose syrup, hydrogenated glucose syrup, and the like, alone or in combination. These sugar sweeteners may also be included as a humectant.

The sweetener can be used in combination with sugarless sweeteners. Generally, sugarless sweeteners include components with sweetening characteristics but which are devoid of the commonly known sugars and comprise, but are not limited to, sugar alcohols, such as sorbitol, mannitol, xylitol, hydrogenated starch hydrolyzates, maltitol, isomalt, erythritol, lactitol and the like, alone or in combination. These sugarless sweeteners may also be included as a humectant.

In an embodiment of the invention the pouch comprises flavor. Flavor may typically be present in amounts between 0.01 and 10% by weight of the total composition of the pouch, such as between 0.01 and 5% by weight of the total composition.

Non-exhaustive examples of flavors suitable in embodiments of the present invention are coconut, coffee, chocolate, vanilla, grape fruit, orange, lime, menthol, liquorice, caramel aroma, honey aroma, peanut, walnut, cashew, hazelnut, almonds, pineapple, strawberry, raspberry, tropical fruits, cherries, cinnamon, peppermint, wintergreen, spearmint, eucalyptus, and mint, fruit essence such as from apple, pear, peach, strawberry, apricot, raspberry, cherry, pineapple, and plum essence. The essential oils include peppermint, spearmint, menthol, eucalyptus, clove oil, bay oil, anise, thyme, cedar leaf oil, nutmeg, and oils of the fruits mentioned above.

In various embodiments of the invention, the matrix composition comprises a release controlling composition for controlling the release of the matrix composition and/or parts thereof, especially the one or more cannabinoids.

The release controlling composition may, according to various embodiments, be selected group consisting of metallic stearates, modified calcium carbonate, hydrogenated vegetable oils, partially hydrogenated vegetable oils, polyethylene glycols, polyoxyethylene monostearates, animal fats, silicates, silicates dioxide, talc, magnesium stearates, calcium stearates, fumed silica, powdered hydrogenated cottonseed oils, hydrogenated vegetable oils, hydrogenated soya oil and mixtures thereof. Particularly, metallic stearates, such as magnesium stearate may be advantageous.

The release controlling composition may be added to the matrix composition in various ways.

For example, the release controlling composition may be added by full powder mixture during the last few minutes of the final mixing.

Alternatively, the release controlling composition may be added after the granulation steps on a granulation premix.

Still further, the release controlling composition may be added only as a fraction of the matrix composition so two different release profiles of cannabinoids is achieved. Even further two or more fractions of the matrix composition may comprise different amounts of the release controlling composition, if any, thereby providing a more complex and tailored release profile of cannabinoids.

The release controlling composition, such as magnesium stearate, may have a sealing effect and can be used to control the release of the one or more cannabinoids and the solubility of the matrix composition.

According to an embodiment of the invention, the pouch comprises polyvinylpyrrolidone (PVP).

One advantage of the above embodiment may be that a more uniform composition may be obtained.

According to an advantageous embodiment of the invention the matrix composition comprises a pH controlling agent. For example, the pH controlling agent may comprise or be a buffering agent.

EXAMPLES

The following examples are illustrative of the present invention and should not be considered as limiting the scope of the invention.

Examples 1-3 illustrate various raw materials and methods for preparing intermediate ingredients.

Examples 4-8 discloses a number of different pouches and their respective compositions.

Example 1

Preparation of Cannabinoid Powder Composition

Cannabinoids come in different grades and form from paste, oil and crystals and in different concentrations. Depending on the form of cannabinoids the manufacturing steps will vary.

As illustrated in the following examples, cannabinoids can be added as powder or sorbed, mixed or granulated on different carriers as sugar alcohols etc.

Example 2

Preparation of Pouches Designed for Administration of Cannabinoids

The material of the pouches is heat sealable non-woven cellulose.

The powder is filled into pouches and is maintained in the pouch by a sealing.

Example 3

Preparation of Pouches with Water-Soluble Composition

Cannabinoids used in example 3 are obtained in accordance with example 1. The pouches described in example 2 are used.

Herein, target fill weight 400 mg powder per pouch. Alternatively, target fill weights of e.g. 250 mg or 800 mg could be used.

Example 3.1

The ingredients are weighed and mixed in a Turbula mixer at 30 RPM to obtain a final powder composition. The obtained final powder composition is manually filled into pouches (target fill weight 400 mg powder per pouch). The pouch of example 2, made from long fiber paper, is used.

When the cannabinoids are supplied as a paste or an oil, the cannabinoids are mixed with about 10 percent by weight of the sugar alcohols to form a granulation solution. The resulting granulate is sieved and placed on a tray. The resulting powder is dried at ambient temperature overnight and is thereafter sieved to obtain a premix composition.

The premix composition is mixed with the remaining ingredients in a Turbula mixer at 30 RPM to obtain a final powder composition.

Magnesium stearate, if any, is added by full powder mixture during the last few minutes of the final mixing. When including smaller amounts of further humectants, apart from e.g. sugar alcohols, these further humectants are added in the same manner as magnesium stearate.

Example 3.2

The cannabinoids are dissolved in ethanol with a weight ratio of about 1:1 to form a homogeneous granulation solution.

The granulation solution is slowly added to the sugar alcohol (e.g. sorbitol, xylitol, maltitol, isomalt, mannitol, or mixtures thereof) powder under stirring (Kitchenaid mixer operated at about 30 RPM in about 30 minutes). The resulting granulate is sieved and placed on a tray. The resulting powder is dried at ambient temperature overnight and is thereafter sieved to obtain a premix.

The obtained premix is mixed with the remaining ingredient to obtain a final powder composition, which is manually filled into pouches (target fill weight 400 mg powder per pouch). The pouch of example 2, made from long fiber paper, is used.

Magnesium stearate, if any, is added by full powder mixture during the last few minutes of the final mixing. When including smaller amounts of further humectants, apart from e.g. sugar alcohols, these further humectants are added in the same manner as magnesium stearate.

Example 3.3

The cannabinoids are dissolved in ethanol with a weight ratio of about 1:1 and the Kollidon 25 (polyvinylpyrrolidone) is added together with the liquid flavor to form a homogeneous granulation solution.

The following solid components are mixed and sieved to form a powder mixture: sugar alcohol (e.g. sorbitol, xylitol, maltitol, isomalt, mannitol, or mixtures thereof), high intensive sweetener, and flavors.

The granulation solution is slowly added to the powder mixture under stirring (Kitchenaid mixer operated at about 30 RPM in about 30 minutes). The resulting granulate is sieved and placed on a tray. The resulting powder is dried at ambient temperature overnight and is thereafter sieved to obtain a final powder composition.

The obtained final powder composition is manually filled into pouches (target fill weight 400 mg powder per pouch). The pouch of example 2, made from long fiber paper, is used.

Magnesium stearate, if any, is added by full powder mixture during the last few minutes of the final mixing. When including smaller amounts of further humectants, apart from e.g. sugar alcohols, these further humectants are added in the same manner as magnesium stearate.

Example 4

Preparation of Pouches with Water-Soluble Compositions

TABLE 1

Cannabinoid pouch; CBD used is a 50% extract. *5% CBD corresponds to 10 mg CBD/pouch. Pouches contain 400 mg per piece.

| | Pouch no. | | | | | | |
|---|---|---|---|---|---|---|---|
| | 101 | 102 | 103 | 104 | 105 | 106 | 107 |
| Method example | 3.1 | 3.1 | 3.1 | 3.1 | 3.1 | 3.2 | 3.3 |
| Raw material | Content in weight percent | | | | | | |
| CBD extract | 5.00* | 5.00* | 5.00* | 5.00* | 5.00* | 5.00* | 5.00* |
| Sorbitol | 93.45 | — | — | — | — | — | — |
| Xylitol | — | 93.45 | — | — | — | — | — |
| Maltitol | — | — | 93.45 | — | — | — | — |
| Isomalt | — | — | — | 93.45 | — | — | — |
| Mannitol | — | — | — | — | 93.45 | 93.45 | 85.45 |
| Flavor | 1.50 | 1.50 | 1.50 | 1.50 | 1.50 | 1.50 | 1.50 |
| HIS | 0.05 | 0.05 | 0.05 | 0.05 | 0.05 | 0.05 | 0.05 |
| PVP | — | — | — | — | — | — | 8.00 |
| Total | 100 | 100 | 100 | 100 | 100 | 100 | 100 |

HIS=High intense sweetener is sucralose. Flavor is pepper mint flavor. PVP=polyvinylpyrrolidone, Kollidon 25.

As can be seen from table 1, different possible water-soluble compositions (here different sugar alcohols) may be used.

Example 5

Preparation of Pouches with Magnesium Stearate

TABLE 2

Cannabinoid pouch; CBD used is a 50% extract.

| Pouch no. | 108 | 109 |
|---|---|---|
| Method example | 3.2 | 3.2 |
| Raw material | Content in weight percent | |
| CBD extract | 5.00* | 5.00* |
| Mannitol | 88.45 | 83.45 |
| Flavour | 1.50 | 1.50 |
| HIS | 0.05 | 0.05 |
| MgSt | 5.00 | 10.00 |
| Total | 100 | 100 |

*5% CBD corresponds to 10 mg CBD/pouch. Pouches contain 400 mg per piece. HIS = High intense sweetener may for example be sucralose. Flavor may for example be pepper mint flavor. MgSt is magnesium stearate and is added as a releasing controlling composition.

As shown in table 2, magnesium stearate (MgSt) can be included in the pouch in different amounts.

Magnesium stearate has a sealing effect and can be used to control the release of CBD and the solubility of the matrix composition.

It is noted that pouch 106 from example 4 may be comparable to pouches 108, 109, only having no MgSt.

Example 6

Preparation of Pouches with Different Cannabinoids and Different Purifications

TABLE 3

Cannabinoid pouch; CBD used corresponds to 10 mg CBD/pouch.

| Pouch no. | 110 | 111 | 112 | 113 | 114 |
|---|---|---|---|---|---|
| Method example | 3.2 | 3.2 | 3.2 | 3.2 | 3.2 |
| Raw material | Content in weight percent | | | | |
| CBD pure (99.5%) | 2.51 | — | — | — | 2.51 |
| CDB extract (50%) | — | 5.00 | — | — | — |
| CDB extract (10%) | — | — | 25.00 | — | — |
| THC pure (99.5%) | — | — | — | 2.51 | 2.51 |
| Mannitol | 95.94 | 93.45 | 73.45 | 95.94 | 88.43 |
| Flavour | 1.50 | 1.50 | 1.50 | 1.50 | 1.50 |
| HIS | 0.05 | 0.05 | 0.05 | 0.05 | 0.05 |
| MgSt | — | — | — | — | 5.00 |
| Total | 100 | 100 | 100 | 100 | 100 |

THC used corresponds to 10 mg THC/pouch. Pouches contain 400 mg per piece. HIS = High intense sweetener may for example be sucralose. Flavor may for example be pepper mint flavor. MgSt is magnesium stearate and is added as a releasing agent.

As seen from table 3, different cannabinoids, CBD and THC, may be used. Also, different concentrations of the cannabinoids may be used, here illustrated as 10% extract, 50% extract, or 99.5% pure cannabinoids. Finally, different cannabinoids may be combined, here shown by a combination of CBD and THC.

Example 7

Preparation of Pouches with Different Concentrations of Cannabinoids when Using Pure CBD (99.5%):

TABLE 4

Cannabinoid pouch; CBD is used in different dosage from 5-100 mg CBD/pouch - CBD extract of 99.5% has been used. Pouches contain 400 mg per piece.

| Pouch no. | 115 | 116 | 117 | 118 | 119 |
|---|---|---|---|---|---|
| Method example | 3.3 | 3.3 | 3.3 | 3.3 | 3.3 |
| Amount of cannabinoids | 5 mg | 10 mg | 20 mg | 50 mg | 100 mg |
| Raw material | Content in weight percent | | | | |
| CDB | 1.26 | 2.51 | 5.03 | 12.56 | 25.13 |
| Isomalt | 84.19 | 82.94 | 80.42 | 72.89 | 60.32 |
| Flavour | 1.50 | 1.50 | 1.50 | 1.50 | 1.50 |
| HIS | 0.05 | 0.05 | 0.05 | 0.05 | 0.05 |
| PVP | 8.00 | 8.00 | 8.00 | 8.00 | 8.00 |
| MgSt | 5.00 | 5.00 | 5.00 | 5.00 | 5.00 |
| Total | 100 | 100 | 100 | 100 | 100 |

HIS = High intense sweetener may for example be sucralose. Flavor may for example be pepper mint flavor. MgSt is magnesium stearate and is added as a releasing agent. CBD could be replaced with THC or be in combination with THC. PVP = polyvinylpyrrolidone, Kollidon 25.

When Using CBD (50% Pure):

TABLE 5

Cannabinoid pouch; CBD is used in different dosage from 5-100 mg CBD/pouch - CBD extract of 99.5% has been used. Pouches contain 400 mg per piece.

| Pouch no. | 120 | 121 | 122 | 123 | 124 |
|---|---|---|---|---|---|
| Method example | 3.3 | 3.3 | 3.3 | 3.3 | 3.3 |
| Amount of cannabinoids | 5 mg | 10 mg | 20 mg | 50 mg | 100 mg |
| Raw material | Content in weight percent | | | | |
| CDB | 2.50 | 5.00 | 10.00 | 25.00 | 50.00 |
| Isomalt | 82.95 | 80.45 | 75.45 | 60.45 | 35.45 |
| Flavour | 1.50 | 1.50 | 1.50 | 1.50 | 1.50 |
| HIS | 0.05 | 0.05 | 0.05 | 0.05 | 0.05 |
| PVP | 8.00 | 8.00 | 8.00 | 8.00 | 8.00 |
| MgSt | 5.00 | 5.00 | 5.00 | 5.00 | 5.00 |
| Total | 100 | 100 | 100 | 100 | 100 |

HIS = High intense sweetener may for example be sucralose. Flavor may for example be pepper mint flavor. MgSt is magnesium stearate and is added as a releasing agent. CBD could be replaced with THC or be in combination with THC. PVP = polyvinylpyrrolidone, Kollidon 25.

As shown in tables 4-5, different total amounts of cannabinoids (here CBD) may be used in the pouch, regardless of using relatively pure cannabinoids or if using an extract comprising other components.

Example 8

Preparation of Pouches with Humectants

TABLE 6

Cannabinoid pouch; CBD used is a 50% extract.

| Pouch no. | 125 | 126 | 127 | 128 |
|---|---|---|---|---|
| Method example | 3.2 | 3.2 | 3.2 | 3.2 |
| Raw material | Content in weight percent | | | |
| CBD extract | 5.00* | 5.00* | 5.00* | 5.00* |
| Isomalt | 93.45 | 91.45 | 91.45 | 91.45 |
| Flavour | 1.50 | 1.50 | 1.50 | 1.50 |
| HIS | 0.05 | 0.05 | 0.05 | 0.05 |
| Glycerol | — | 2.00 | — | — |
| Sodium alginate | — | — | 2.00 | — |
| Pectin | — | — | — | 2.00 |
| Total | 100 | 100 | 100 | 100 |

*5% CBD corresponds to 10 mg CBD/pouch. Pouches contain 400 mg per piece. HIS = High intense sweetener may for example be sucralose. Flavor may for example be pepper mint flavor. Glycerol, sodium alginate and pectin are acting as humectants.

As shown in table 6, different further humectants may be added. Humectants attract the saliva from the mouth and make sure that water is available in the pouch. Increased water increase the release.

Example 9

Evaluation

The pouches produced were evaluated and found highly suitable as delivery vehicles for cannabinoids.

The invention claimed is:

1. A pouch designed for administration of an active ingredient in the oral cavity, the pouch containing a matrix composition comprising:
    powdered granules comprising
        one or more cannabinoids and
        a water soluble composition, wherein the one or more cannabinoids is released from the matrix composition within 10 minutes.

2. The pouch according to claim 1, wherein the water-soluble composition comprises a water-soluble carrier.

3. The pouch according to claim 1, wherein the water-soluble composition comprises sugar alcohol.

4. The pouch according to claim 3, wherein said sugar alcohol is selected from the group consisting of sorbitol, erythritol, xylitol, lactitol, maltitol, mannitol, hydrogenated starch hydrolysates, isomalt and any combination thereof.

5. The pouch according to claim 1, wherein the water-soluble composition comprises sugar.

6. The pouch according to claim 1, wherein the matrix composition further comprises a release controlling composition.

7. The pouch according to claim 6, wherein said release controlling composition comprises one or more metallic stearates.

8. The pouch according to claim 6, wherein said release controlling composition comprises magnesium stearate.

9. The pouch according to claim 6, wherein said release controlling composition comprises calcium stearate.

10. The pouch according to claim 6, wherein the matrix composition comprises said release controlling composition in an amount of between 1 and 20 percent by weight of said matrix composition.

11. The pouch according to claim 1, wherein the pouch comprises a woven or non-woven fabric.

12. The pouch according to claim 1, wherein the one or more cannabinoids is physically or chemically bound to at least part of the matrix composition acting as a carrier.

13. The pouch according to claim 12, wherein the one or more cannabinoids has been granulated with the carrier.

14. The pouch according to claim 1, wherein the matrix composition comprises said one or more cannabinoids in an amount of between 0.1 and 50 percent weight of said matrix composition.

15. The pouch according to claim 1, wherein said one or more cannabinoids comprises cannabidiol.

16. The pouch according to claim 1, wherein said one or more cannabinoids comprises cannabidiol in an amount of between 10 and 100 percent by weight of the one or more cannabinoids.

17. The pouch according to claim 1, wherein said one or more cannabinoids comprises tetrahydrocannabinol.

18. The pouch according to claim 1, wherein the one or more cannabinoids comprises tetrahydrocannabinol in an amount of between 10 and 100 percent by weight of the one or more cannabinoids.

19. The pouch according claim 1, wherein the pouch comprises a humectant.

20. A pouch designed for administration of an active ingredient in the oral cavity, the pouch containing a water-soluble matrix composition comprising an amount of one or more cannabinoids present in granules of the water-soluble matrix composition, and wherein the one or more cannabinoids is released from the matrix composition within 10 minutes.

21. A pouch designed for administration of an active ingredient in the oral cavity, the pouch containing:
   a matrix compositing comprising
      one or more cannabinoids and
      one or more sugar alcohols; and
   a release controlling composition, and wherein the one or more cannabinoids is released from the matrix composition within 10 minutes.

22. The pouch according to claim 21, wherein the one or more cannabinoids have been granulated with the one or more sugar alcohols.

* * * * *